United States Patent [19]

Lewis et al.

[11] 4,455,389

[45] Jun. 19, 1984

[54] MAGNESIUM HYDRIDE MODIFIED ALUMINUM/SILICEOUS COMPOSITIONS

[75] Inventors: Robert M. Lewis, Sugarland; Lynn H. Slaugh, Cypress, both of Tex.

[73] Assignee: Shell Oil Company, Houston, Tex.

[21] Appl. No.: 477,185

[22] Filed: Mar. 21, 1983

[51] Int. Cl.³ .................. B01J 21/08; B01J 29/00; B01J 21/10; B01J 23/08

[52] U.S. Cl. .................. 502/232; 502/240; 502/250; 502/251; 502/341

[58] Field of Search ............... 252/451, 455 R; 502/341, 250

[56] References Cited

U.S. PATENT DOCUMENTS

| | | | |
|---|---|---|---|
| 2,188,007 | 1/1942 | Kistler | 252/451 X |
| 2,281,919 | 5/1942 | Connolly | 252/451 X |
| 2,680,100 | 6/1954 | Elston | 252/451 |
| 2,699,430 | 1/1955 | Teter | 252/451 X |
| 2,731,452 | 1/1956 | Field et al. | 252/458 X |
| 2,852,576 | 9/1958 | Fotis et al. | 252/455 R |
| 2,900,349 | 8/1959 | Schwartz | 252/451 X |
| 2,935,483 | 5/1960 | Schwartz | 252/455 R |
| 2,958,648 | 11/1960 | Braithwaite | 252/465 R X |
| 3,526,601 | 9/1970 | Fotis, Jr. et al. | 252/465 X |
| 3,893,943 | 7/1975 | Willard, Sr. | 252/451 X |
| 4,235,756 | 11/1980 | Slaugh | 252/463 |
| 4,239,872 | 12/1980 | Slaugh | 252/464 X |
| 4,295,999 | 10/1981 | Slaugh | 252/458 X |
| 4,367,361 | 1/1983 | Slaugh | 585/532 X |
| 4,368,342 | 1/1983 | Slaugh | 585/457 X |
| 4,375,574 | 3/1983 | Slaugh | 585/474 |
| 4,375,575 | 3/1983 | Slaugh | 585/481 X |
| 4,384,154 | 5/1983 | Slaugh | 585/415 |

Primary Examiner—Delbert E. Gantz
Assistant Examiner—William G. Wright

[57] ABSTRACT

Novel compositions are prepared by reacting magnesium hydride and metal oxide gels in the slurry phase. These compositions are useful as catalysts and catalyst supports.

8 Claims, 1 Drawing Figure

MAGNESIUM HYDRIDE MODIFIED ALUMINUM/SILICEOUS COMPOSITIONS

FIELD OF THE INVENTION

This invention relates to novel aluminous, alumino-siliceous, and siliceous compositions modified with magnesium hydride. These compositions are useful as catalysts and supports, particularly as supports for syngas catalysts.

BACKGROUND OF THE INVENTION

Aluminas, silicas and alumino-silicas find frequent use as catalysts and as supports for catalyst metals. The support itself can in many instances modify the catalyzed reaction. Modifications of the support can thus effect the catalyst activity and selectivity as well as change the product mix. Various means have been utilized to add modifiers to supports. A frequently used method is to impregnate the support with dissolved salt or compound and then calcine the impregnated material.

In Russian Inventors' Certificate No. 584,886 there is disclosed the preparation of supported niobium hydride catalysts. In this reference, however, the hydride is not reacted with the support, but exists as the unreacted hydride on the support.

In U.S. Pat. No. 3,146,209 issued Aug. 25, 1964, a solution of etherated aluminum hydride is used to react with a metal oxide gel substrate.

In U.S. Pat. No. 4,235,756 issued Nov. 25, 1980 and U.S. Pat. No. 4,335,022 issued June 15, 1982 a solution of aluminum hydride is used to impregnate an alumina gel or a silica gel which is subsequently calcined.

SUMMARY OF THE INVENTION

This invention relates to novel metal oxide gel compositions. These compositions have been modified with magnesium hydride and find use as catalysts and as catalyst supports. In general, they are prepared by contacting a substantially anhydrous metal oxide gel with a powdered magnesium hydride in the slurry phase wherein the slurrying medium is an anhydrous, non-hydroxyl containing organic liquid wherein preferably the amount of magnesium hydride utilized is not greater than the amount needed to completely react with hydroxyl moieties present in the metal oxide gel. After contact and reaction with the hydride, the metal oxide gel is dried to remove the solvent and optionally calcined at elevated temperatures.

BRIEF DESCRIPTION OF THE DRAWING

The sole drawing illustrates the use of the instant compositions as catalyst supports for ruthenium catalyzed syngas reactions. Curve A uses magnesia-modified silica compositions of the instant invention. Curve B uses magnesia-silica prepared using conventional magnesium nitrate impregnation techniques. Curve C uses pure silica.

DESCRIPTION OF THE PREFERRED EMBODIMENTS

Figure 1:
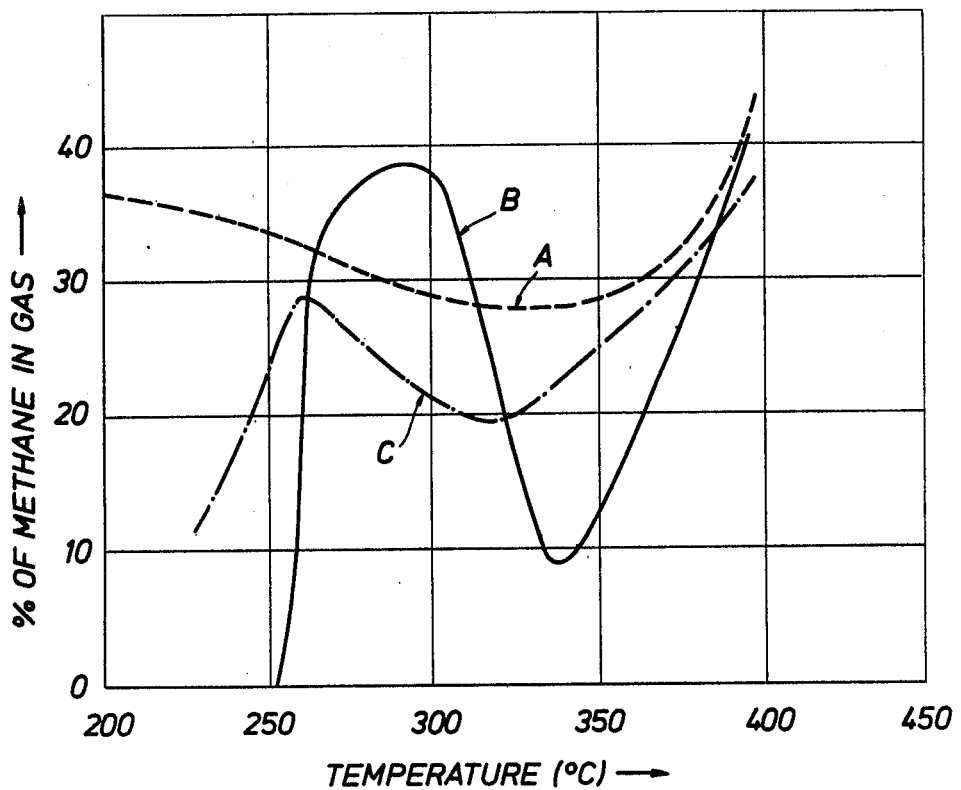

The gel oxides suitable for use in preparing the compositions of the instant inventions are any of the metal oxide gels that are well known in the catalytic art useful as either catalyst base materials or as promoting materials in catalyst compositions. Additionally, the term "metal oxide gel" as used herein shall also include the plural oxide gels, i.e., those that contain mixtures or compounds of two or more metal oxides. A metal oxide gel is basically a metal oxide that contains chemically bound water in the form of hydroxyl groups. Upon calcination at sufficiently elevated temperatures, water is given off and the gel is converted to the oxide with two hydroxyl moieties giving one molecule of water and an oxygen is attached to a metal ion. Illustrative of gel oxide base materials used to prepare the composition of this invention are aluminas, silicas, alumina-silicas, alumina-zirconias, silica-zirconias and the like, including naturally occurring hydrous oxide minerals such as clays. Preferred oxide gel materials are selected from the group consisting of alumina, silica and alumina-silica.

Prior to use the metal oxide gels should be substantially free of absorbed water, i.e., "substantially dehydrated or anhydrous". The absorbed or free water is removed by heating the gels at temperatures ranging from about 100° C. to about 900° C. prior to contact with the hydride. Any environment that provides for drying is suitable such as air, vacuum, inert gas such as nitrogen, etc. The dried gels should be kept away from a humid atmosphere after drying. It is understood that a dried gel will still contain chemically bound water in the form of hydroxide and hydroxyoxide.

An aluminum oxide gel is one of the preferred substrates. This alumina can be any of the variety of available aluminas. These are commercially available under various names such as alumina gels, activated aluminas, gamma aluminas, etc. Regarding purity of the alumina, it may be stated that small amounts of impurities are not generally detrimental, and may be beneficial when the impurity is present as a cogel. In fact "impurities" may be purposely added for catalytic effects. The following table lists several commercial aluminas and their properties which are found suitable.

| Alumina | Surface Area, $m^2g$ | Pore Vol., cc/gm | Na, ppm | $SO_4^=$ % wt | $Fe_2O_3$ % wt | $Cl^-$ % wt |
|---|---|---|---|---|---|---|
| CCI[a] | 252 | 0.8 | 160 | 0.06 | — | 0.02 |
| KA-209[b] | 365 | 0.42 | 600 | 0.03 | — | 0.01 |
| RA-1[c] | 263 | 0.26 | 4700 | 0.02 | 0.18 | — |
| ACCO[d] | 225 | 0.68 | 580 | 0.6 | — | 0.6 |
| Norton | 218 | 0.62 | 0.51 | 0.03 | — | 0.03 |

[a]Catalysts & Chemicals, Inc., now United Catalysts
[b]Kaiser
[c]Reynolds Corp.
[d]American Cyanamid Corp.
[e]Conoco Corp.
[f]Filtrol Corp.

Silica gel is also another preferred substrate. These are readily available commercially and are essentially substantially dehydrated amorphous silica. These materials are available in various density grades, from low density with surface areas ranging from about 100–200 $m^2/g$ to regular density with surface areas up to about 800 $m^2/g$. The commercially available materials are used as dessicants, selective absorbents, catalysts and catalyst supports. Regarding purity of the silica, it may be stated that small amounts of impurities are not generally detrimental and may be beneficial when the impurity is present as a co-gel. In fact, "impurities" may be purposely added for catalytic effects. The following table lists several commercial silicas and their properties which are found suitable.

| Support | Surface Area, m²/g | Pure Vol, cc/g | Density g/cc | Particle Size |
|---|---|---|---|---|
| Davison* Grade 952 SiO₂ | 300 | 1.65 | 0.35 | 70 mesh (avg) |
| Davison Grade 57 SiO₂ | 300 | 1.0 | 0.4 | 100 mesh |
| Davison Grade 03 SiO₂ | 750 | 0.43 | 0.7 | 8 mesh (avg) |

*Manufactured by Davison Chemical Div., W. R. Grace & Co.

Other preferred substrates are the alumino-silicates. These materials contain various mixtures of aluminum and silicon oxides. They are readily available commercially and are generally employed as cracking catalysts. Typically they contain from about 50 to about 95, preferably from about 70 to about 90 percent by weight of silica. Illustrations of commercially available alumina-silicas are Davison Grade 980-25 (manufactured by Davison Chemical Division, W. R. Grace & Co.) which contains about 75% $SiO_2$ and 25% $Al_2O_3$ and Davison Grade 980-13 which contains about 87% $SiO_2$ and 13% $Al_2O_3$. These materials can be prepared in a conventional fashion, as for example by co-precipitation, co-gellation, or by spray drying.

In general, the compositions of the instant invention are prepared by contacting the substrate with magnesium hydride in a slurry phase and allowing the hydride to react with the substrate, which reaction is evidenced by the evolution of hydrogen gas. The temperature of contact is not critical and is generally made at room temperature, although higher or lower temperatures are not precluded. In general contact temperatures of about 0°–100° C. are utilized. After reaction, the magnesium is present in and on the metal oxide gel in the form of an oxide or oxygen-containing compound of magnesium complexed with the metal oxide(s) of the gel, although the exact form of the magnesium oxide is not known.

The magnesium hydride used to prepare the slurry is readily available commercially. It can be prepared in various ways. It has been prepared by lithium aluminum hydride reduction of magnesium compounds and by pyrolysis of alkyl magnesiums. A preferred commercial method of preparation is by synthesis from the elements using special ball-milling techniques to provide a continuous fresh surface and careful control of temperatures of hydrogen pressure. To prepare the slurry, the magnesium hydride is ground to a fine powder, for example, less than 60, preferably less than 100 mesh and then mixed with an anhydrous, nonhydroxyl-containing organic solvent. Both water and hydroxylic materials react with the magnesium hydride and therefore during the processing of the compositions of the instant invention, contact with water, and other hydroxyl-containing materials should be avoided. However, once the compositions are prepared by reaction with the magnesium hydride, they are no longer sensitive to water and other hydroxyl-containing materials. The inert solvent used to prepare the slurry of magnesium hydride should be a solvent that is inert to magnesium hydride. Suitable solvents include alkanes such as hexane, cyclohexane, heptane, dodecane, etc., ethers, such as dimethyl ether, diethyl ether, tetrahydrofuran, etc., and ketones such as dimethyl ketone, methylisobutyl ketone, methylethyl ketone, etc.

In general, an amount of magnesium hydride is used to react with the substrate in an amount that does exceed that amount that is needed to completely react with the hydroxyl moieties present in the metal oxide gel substrate, i.e., an excess of hydride is not used, although lesser amounts than necessary to completely react with the substrate are frequently used. If amounts of magnesium hydride greater than that needed to completely react with the hydroxyl moieties present in the substrate is utilized, then upon completion of the reaction, excess magnesium hydride would be left on the substrate. This "free" magnesium hydride would be converted to magnesium oxide or hydroxide upon contact with hydroxyl-containing materials or by calcination in air at elevated temperatures, but would be in a different form from the magnesium oxide prepared by the reaction of the hydride with the substrate. Thus, the use of excess magnesium hydride would provide a composition according to the instant invention which would also contain "free" (i.e., unreacted with the substrate) magnesium hydride, hydroxide or oxide. In general, the composition of the instant invention will contain from about 0.001 to about 50, preferably from about 0.01 to about 25 and most preferably from about 0.1 to about 10 percent by weight of magnesium measured as the metal.

In a preferred embodiment, the instant compositions are prepared by adding powdered magnesium hydride to a slurry of metal oxide gel particles under dry box conditions. Alternatively, the metal oxide gel particles can be added to a slurry of magnesium hydride powder. The resultant mixture is stirred until reaction has ceased as indicated by the cessation of hydrogen evolution. After reaction, the compositions are filtered and dried to remove the solvent. Optionally, the compositions are frequently calcined at temperatures ranging from about 200° C. to 900° C. prior to use as catalysts or catalyst supports.

The compositions of the instant invention can be utilized as catalysts and as catalyst supports. The magnesium modified materials have different physical and chemical properties than the unmodified materials or materials modified using other magnesium compounds. For example, the instant compositions have physical characteristics and properties that differ from those materials prepared for example, by impregnating substrates with magnesium nitrate and calcining. To illustrate this difference three samples were prepared. Sample 1 was prepared according to this invention as described in the following Illustrative Embodiments. Sample 2 was also prepared as described in the following Illustrative Embodiment, but was subsequently calcined at elevated temperature. Sample 3 was prepared by impregnating alumina with an aqueous solution of magnesium nitrate, drying and calcining the resultant material at elevated temperatures similar to those of Sample 2 X-Ray photoelectron spectroscopy (XPS) was used to determine the surface distribution of magnesium on the surface of the samples. The samples were prepared for analysis by grinding in an argon atmosphere, followed by mounting on polymer tape. The XPS spectra were recorded on a Varian IEE spectrometer. The relative number of atoms seen on the surface of the compositions using x-ray photoelectric spectroscopy was determined from the core level spectra for the 1s level of magnesium and the 2s level of aluminum. Table 1 shows the results as the ratios of the relative intensities of the magnesium's 1s element line to the aluminum's 2s element line.

TABLE 1

| Surface Atomic Concentrations | |
|---|---|
| | Mg 1s/Al 2s |
| Sample 1: Ex MgH$_2$, 3.3% Mg on Al$_2$O$_3$ | 1.6 |
| Sample 2: Ex MgH$_2$, 3.3% Mg on Al$_2$O$_3$ Calcined | 2.9 |
| Sample 3: Ex Mg(NO$_3$)$_2$ 3.5% Mg on Al$_2$O$_3$ Calcined | 0.15 |

As can be seen from Table 1, the compositions according to this invention have the magnesium distributed over the surface in a significantly different manner than the conventionally prepared magnesium nitrate impregnated material.

The compositions of the instant invention and their use as catalysts will be further described below by the following illustrative embodiments which are provided for illustration and are not to be construed as limiting the invention.

ILLUSTRATIVE EMBODIMENTS

Composition Preparation

The following example illustrates the preparation of compositions according to the instant invention.

In a dry box, magnesium hydride powder (0.82 g; less than about 100 mesh) was added with stirring to a slurry of calcined Kaiser KA 201 Alumina (33 g, 20–30 mesh) in dry tetrahydrofuran (80 ml). Stirring was continued for a period of 2 days in a sealed vessel. At the end of the 2 day period the flask was opened and the tetrahydrofuran was allowed to evaporate. The resultant composition contained about 2.5% wt magnesium measured as the metal.

A similar composition was prepared using the technique described above and Davison Grade 57 Silica.

Utilization of Composition as Catalyst Support

A sample of a magnesia-silica composition prepared as described above was dried under high vacuum and pelletized to 20–30 mesh size. The composition (2.6 g, 9 ml) was impregnated with a solution of ruthenium trichloride in water (0.5 g of ruthenium salt containing 47.5% ruthenium in 3.8 ml deionized water). This gave about 8.9% weight ruthenium on the support.

The impregnated support was calcined in a quartz tube by heating to 250° C. under nitrogen gas flow (500 cc/min) for 4 hours.

The calcined catalyst was transferred to a 1.4 cm ID highpressure 316 stainless steel tubular reactor. Silicon carbide chips (15 ml each) were used above and below the catalyst to support it in the center of the reactor.

The catalyst was reduced by hydrogen at 900 psig and a flow of 500 cc/min. by heating the reactor over a 2 hour period to 450° C. and holding at 450° C. for an additional 2 hour period.

The reactor was allowed to cool to room temperatured and carbon monoxide and hydrogen in a 1:1 molar ratio was passed over the catalyst at 500 cc/min (GHSV about 3000). The reactor was then heated to the desired temperature. The weight of methane in the product was determined and is plotted in the FIGURE as Curve A as a function of temperature.

A ruthenium catalyst was made as described above but using as a support Davison Grade 57 Silica which had been impregnated with an aqueous solution of magnesium nitrate and subsequently calcined. This catalyst was tested as above and the results are shown in the FIGURE as Curve B.

The above was repeated using as a support untreated Davison Grade 57 Silica. The results are shown as Curve C in the FIGURE.

As can be seen from the FIGURE the composition of the instant invention when used as supports provide different catalytic responses as a function of temperature than do untreated silica and silica impregnated with magnesium nitrate and subsequently calcined.

We claim:

1. A process for preparing a metal oxide gel composition having bonded thereto a magnesium oxide, which process comprises contacting a substantially anhydrous metal oxide gel with a powdered magnesium hydride in a slurry phase with slurrying medium being an anhydrous, non-hydroxyl-containing organic liquid whereby the magnesium hydride reacts with the metal oxide gel, and subsequently drying the gel to remove the organic liquid.

2. The process of claim 1 wherein the metal oxide gel is selected from the group consisting of aluminum oxide gel, silicon oxide gel and aluminum-silicon oxide gel.

3. The process of claims 1 or 2 wherein the amount of magnesium hydride utilized is not greater than the amount needed to completely react with hydroxyl moieties present in this metal oxide gel.

4. The process of claims 1 or 2 wherein the slurrying liquid is tetrahydrofuran.

5. The process of claims 1 or 2 wherein the magnesium hydride powder is less than about 100 mesh in size.

6. The process of claims 1 or 2 wherein, after drying, the gel is calcined at a temperature ranging from about 200° C. to about 900° C.

7. The process of claims 1 or 2 wherein the magnesium in the composition ranges from about 0.001 to about 50 percent by weight measured as magnesium metal.

8. The process of claims 1 or 2 wherein the magnesium in the composition ranges from about 0.01 to about 25 percent by weight measured as magnesium metal.

* * * * *